(12) United States Patent
Jo (10) Patent No.: US 11,253,344 B2
(45) Date of Patent: Feb. 22, 2022

(54) CUSTOM DENTAL IMPLANT AND METHOD AND SYSTEM FOR MAKING A CUSTOM DENTAL IMPLANT

(71) Applicant: DENTSPLY SIRONA Inc., York, PA (US)

(72) Inventor: Jeremy E. Jo, Somerville, MA (US)

(73) Assignee: DENTSPLY SIRONA INC., York, PA (US)

( * ) Notice: Subject to any disclaimer, the term of this patent is extended or adjusted under 35 U.S.C. 154(b) by 450 days.

(21) Appl. No.: 16/158,370

(22) Filed: Oct. 12, 2018

(65) Prior Publication Data

US 2020/0113656 A1 Apr. 16, 2020

(51) Int. Cl.
| A61C 8/00 | (2006.01) |
| A61B 5/055 | (2006.01) |
| A61B 6/03 | (2006.01) |
| A61B 6/14 | (2006.01) |
| A61B 6/00 | (2006.01) |
| A61C 9/00 | (2006.01) |
| A61C 13/00 | (2006.01) |

(52) U.S. Cl.
CPC ............ *A61C 8/0086* (2013.01); *A61B 5/055* (2013.01); *A61B 6/032* (2013.01); *A61B 6/14* (2013.01); *A61B 6/4085* (2013.01); *A61C 8/0012* (2013.01); *A61C 8/0036* (2013.01); *A61C 8/0037* (2013.01); *A61C 9/0046* (2013.01); *A61C 13/0004* (2013.01); *A61C 13/0006* (2013.01)

(58) Field of Classification Search
CPC ... A61C 8/0033; A61C 8/0036; A61C 8/0037; A61C 8/0043; A61C 8/0086; A61C 2008/0046; A61C 8/0034
See application file for complete search history.

(56) References Cited

U.S. PATENT DOCUMENTS

| 2,721,387 | A | * | 10/1955 | Ashuckian | ............ | A61C 8/0018 |
| | | | | | | 433/173 |
| 3,628,248 | A | * | 12/1971 | Kroder | .................. | A61K 6/891 |
| | | | | | | 433/175 |
| 7,708,557 | B2 | | 5/2010 | Rubbert | | |
| 8,287,279 | B2 | * | 10/2012 | Pirker | .................. | A61C 8/0018 |
| | | | | | | 433/175 |
| 8,602,780 | B2 | | 12/2013 | Rubbert | | |
| 8,911,234 | B2 | | 12/2014 | Mayer | | |
| 9,539,062 | B2 | | 1/2017 | Rubbert | | |
| 9,693,837 | B2 | * | 7/2017 | Lee | ........ | A61C 8/0043 |
| 2007/0264612 | A1 | * | 11/2007 | Mount | ................. | A61C 8/0043 |
| | | | | | | 433/173 |
| 2009/0092944 | A1 | * | 4/2009 | Pirker | ................. | A61C 8/0036 |
| | | | | | | 433/173 |

(Continued)

OTHER PUBLICATIONS

International Search Report; PCT/US2019/055300; Nov. 14, 2019 (completed); dated Nov. 25, 2019.

(Continued)

*Primary Examiner* — Edward Moran
(74) *Attorney, Agent, or Firm* — Dentsply Sirona Inc.

(57) ABSTRACT

A custom dental implant and a method and system for making the custom dental implant having one or more energy storing devices that deflect during installation and expand to provide stability after insertion in a natural dental socket of a patient.

9 Claims, 8 Drawing Sheets

(56) References Cited

U.S. PATENT DOCUMENTS

| | | | | |
|---|---|---|---|---|
| 2013/0273498 A1* | 10/2013 | Woods | ............... | A61C 8/0054 |
| | | | | 433/119 |
| 2013/0323677 A1* | 12/2013 | Pearson | ............ | A61C 8/0036 |
| | | | | 433/173 |
| 2014/0004481 A1* | 1/2014 | Spahn | ................ | A61C 8/0012 |
| | | | | 433/173 |
| 2017/0239020 A1 | 8/2017 | McDonald | | |

OTHER PUBLICATIONS

Written Opinion of the International Searching Authority; PCT/US2019/055300; Nov. 14, 2019 (completed); dated Nov. 25, 2019.

\* cited by examiner

CUSTOM DENTAL IMPLANT AND METHOD AND SYSTEM FOR MAKING A CUSTOM DENTAL IMPLANT

FIELD OF THE INVENTION

The present application relates generally to a spring loaded implant and a method and system for making the spring loaded implant and more specifically to a custom dental implant and a method and system for making the custom dental implant having one or more energy storing devices that may deflect during installation and expand to provide external pressure and therefore an interference fit to achieve stability.

BACKGROUND OF THE INVENTION

Natural teeth in humans may be supported in jawbone by periodontal fibers that function as shock absorbers when a compressive force is applied, such as during chewing. Due to tooth decay, accidental injury, anatomical abnormalities, age, and the like, a natural tooth of a patient may be removed or missing. As a result, dental implant devices may be implanted in the patient's bone structure to improve the patient's physical appearance and/or tooth function. Dental implants widely used in dental treatment are off-the-shelf products. Because teeth may have to fit properly for comfort and healing-process after surgery in the periodontal fibers of a patient, some commonly used implants may not be an optimal replacement.

One type of dental implant is the non-screw type of implant systems an example being a non-screw root form implant system (hereinafter referred to as custom dental implant), wherein an exterior geometry of the implant may be designed to resemble the shape of a natural tooth root. This type of implant systems may preclude conventional dental surgical procedures including multiple drilling sequences. Herein the implant may be placed at the same time as extraction with minimal modification to the dental anatomy.

The installation of such implants may however require the use of significant force to fully seat the implant. In some cases, a hammer may be used. This may originate from the general undercut anatomy of a dental root. A base portion of a dental root may be wider than an upper coronal portion of the dental root, therefore a material of the implant may be wider at the base in order to maintain contact with bone.

Moreover, conventional screwed in implants may rely on the threaded function of the implant to provide initial rotational stability until the implant fully osseointegrates. Non-screw root form implants may not rely on a threaded feature because of the intimate implant to bone contact required by the organic shape of the root. Also, a non-cylindrical geometry does not allow for the use of traditional threads. An interference fit, or press fit of the implant into the socket during placement however provides limited stability. Some non-screw root form implants may rely on the use of a bridge to cover and protect the implant during osseointegration. These bridges may be anchored to neighboring healthy teeth thus limiting use when multiple units are to be placed adjacent to each other.

U.S. Pat. No. 8,602,780B2 discloses a customized dental prosthesis and implant manufactured based on a process that includes copying a significant portion of the original root geometry of a human tooth to be integrated after extraction of the original tooth either in the existing biological cell structure of the periodontal ligament or as one piece into the embedding bone structure of the respective jaw.

U.S. Pat. No. 8,911,234B2 discloses an implant to be implanted in bone tissue, the implant being implanted in a cavity specially created or adjusted for the purpose. For implantation, the implant may be impinged with mechanical oscillations, resulting in the thermoplastic material of parts of the surface being at least partially liquefied and pressed into unevennesses and pores of the cavity wall to form a form-fit and/or material-fit connection between implant and cavity wall, when re-solidified.

U.S. patent application Ser. No. 11/724,261 shows a customized dental prosthesis for osseointegration having a first manufactured portion shaped to substantially conform to the three-dimensional surface of a root of a tooth to be replaced and a second manufactured portion shaped to substantially conform to the three-dimensional surface of a crown of a tooth to be replaced.

U.S. Pat. No. 9,539,062B2 discloses methods of designing and manufacturing customized dental prosthesis including the steps of receiving imaging data such as x-ray image data and surface scan data of a dental anatomy and/or a physical impression of the dental anatomy of a specific patient, forming a three-dimensional virtual model of portions of a non-functional natural tooth positioned in the jawbone of the patient based on the imaging and surface scan data, virtually designing a dental implant based upon the virtual model, exporting the data describing the designed dental implant to a manufacturing machine, and custom manufacturing the dental implant for the specific patient.

SUMMARY OF THE INVENTION

Existing limitations associated with the foregoing, as well as other limitations, may be overcome by a custom dental implant a method and system for making the custom dental implant having an energy storing mechanism that may deflect during installation and expand to provide external pressure and therefore a barbed fit to achieve stability.

According to an aspect of the present invention a custom dental implant may be provided for insertion into a jaw, comprising: an occlusal facing portion constructed to receive a restoration or to form an integral part of the restoration; a mid-portion featuring a contoured shape to mimic the natural profile of gingival emergence for optimal aesthetics; and a bottom/apical portion configured to match or substantially match a shape of a natural extraction socket, the bottom portion including one or more prongs, and at least one energy storing device disposed along or integrated with said mid-portion and/or prongs and configured to deflect during insertion into the natural extraction socket and to expand to provide external pressure to stabilize the custom dental implant in the natural extraction socket during osseointegration, wherein a structure of the at least one energy storing device is based on information such as the tooth number or location of the tooth replacement, the contours and geometry of the alveolar bone, the amount of periodontal ligament fibers present, the initial stability required after implant placement, location of any neighboring nerves or other sensitive dental anatomy, and quality or quantity of bone required for the support of a dental implant device.

According to another aspect of the present invention the custom dental implant may be provided including one or more combinations of the following: (i) wherein the custom dental implant is made of a material that is capable of osseointegrating with the natural bone and are biocompatible, such as titanium, titanium alloys, stainless steel materials and/or ceramic materials, (ii) wherein the at least one energy storing device is made of the same material as an internal portion of the custom dental implant, (iii) wherein the at least one energy storing device is an outer shell or is part of the outer shell of the custom dental implant, (iv) wherein the at least one energy storing device is a spring, coil, or barb, (v) wherein a prong of the custom dental implant is constructed to be flexible in order to bend during insertion into the natural extraction socket, (vi) wherein the custom dental implant and/or the at least one energy storing device is made from resorbable structural material, (vii) wherein the resorbable structural material is hydroxyapatite, tri-calcium phosphate and/or magnesium, (viii) wherein the at least one energy storing device fully or partially surrounds a mid-section and/or prongs of the custom dental implant, (ix) wherein the prongs are configured as beam-like geometries forming the at least one energy storing device, (x) wherein an internal portion is constructed to mimic anti-rotation features, threads and/or connection geometries of screw form dental implants to fit a stock or custom dental abutment, crown, bar, bridge, or similar type of supporting restoration.

According to an aspect of the present invention a method of preparing a custom dental implant may be provided, the method comprising; receiving three dimensional data representing a shape of a natural extraction socket of tooth of a patient; analyzing the three-dimensional data to obtain information about characteristics of the natural extraction socket said information including the anatomy of the extraction site, amount of remaining periodontal ligament, location of nerves, density of surrounding bone, and depth or amount of bone; designing a three-dimensional image of the custom dental implant based on the shape of the natural extraction socket, the three-dimensional image of the custom dental implant having (i) an occlusal facing portion for receiving a restoration or forming an integral part of the restoration, (ii) a mid-portion featuring a contoured shape to mimic the natural profile of gingival emergence for optimal aesthetics, (iii) a bottom portion including one or more prongs and (iv) at least one energy storing device, the at least one energy storing device being provided along or integrated into the three-dimensional image of the custom dental implant, wherein a structure of the at least one energy storing device is based on information such as the tooth number or location of the tooth replacement, the contours and geometry of the alveolar bone, the amount of periodontal ligament fibers present, the initial stability required after implant placement, location of any neighboring nerves or other sensitive dental anatomy, and quality or quantity of bone required for the support of a dental implant device such that the at least one energy storing device deflects during insertion into the natural extraction socket and expands to provide external pressure to stabilize the custom dental implant in the natural extraction socket during osseointegration, and fabricating the custom dental implant based on said designing step.

According to another aspect of the present invention the method may be provided including one or more combinations of the following: (i) further comprising scanning the tooth to obtain the shape of the natural extraction socket prior to receiving the three-dimensional data, (ii) further comprising scanning the tooth before extracting said tooth, (iii) further comprising scanning the tooth after extracting said tooth, (iv) further comprising performing the scanning step with a Computer Tomography (CT), Cone Beam Computed Tomography (CBCT), digital intraoral scan, and/or Magnetic Resonance Imaging (MRI) machine, (v) further comprising inserting the custom dental implant into the natural extraction socket, (vi) further comprising surgically adapting the natural extraction socket before said inserting step, (vii) further comprising designing the at least one energy storing device to fully or partially surrounds a mid-section and/or prongs of the custom dental implant, (viii) further comprising designing the prongs as beam-like geometries which form the at least one energy storing device, (ix) further comprising designing an internal portion to mimic anti-rotation features, threads and/or connection geometries of screw form dental implants.

According to an aspect of the present invention a non-transitory computer-readable medium storing sequences of instructions may be provided, wherein the sequences of instructions include instructions which, when executed by a computer system, cause the computer system to: receive three dimensional data representing the shape of a natural extraction socket of a patient; analyze the three-dimensional data to obtain information about characteristics of the natural extraction socket said information including information such as the tooth number or location of the tooth replacement, the contours and geometry of the alveolar bone, the amount of periodontal ligament fibers present, the initial stability required after implant placement, location of any neighboring nerves or other sensitive dental anatomy, and quality or quantity of bone required for the support of a dental implant device; design a three-dimensional image of the custom dental implant based on the shape of the natural extraction socket, the three-dimensional image of the custom dental implant having (i) an occlusal facing portion for receiving a restoration or forming an integral part of the restoration, (ii) a mid-portion featuring a contoured shape to mimic the natural profile of gingival emergence for optimal aesthetics, (iii) a bottom portion including one or more prongs and (iv) at least one energy storing device, the at least one energy storing device being provided along or integrated into the three-dimensional image of the custom dental implant, wherein a structure of the at least one energy storing device is based on information such as the tooth number or location of the tooth replacement, the contours and geometry of the alveolar bone, the amount of periodontal ligament fibers present, the initial stability required after implant placement, location of any neighboring nerves or other sensitive dental anatomy, and quality or quantity of bone required for the support of a dental implant device such that the at least one energy storing device deflects during insertion into the natural extraction socket expands to provide external pressure to stabilize the custom dental implant in the natural extraction socket during osseointegration.

According to another aspect of the present invention the non-transitory computer-readable medium storing sequences of instructions may be provided may wherein the instructions, when executed by the computer system, further cause the computer system to fabricate the custom dental implant based on the design.

According to an aspect of the present invention a system for designing a custom dental implant may be provided, the system comprising: at least one processor operable to: receive three dimensional data representing the shape of a natural extraction socket of a patient; analyze the three-dimensional data to obtain information about characteristics of the natural extraction socket said information including the anatomy of the extraction site, amount of remaining periodontal ligament, location of nerves, soft tissue geometry and profile, density of surrounding bone, and depth or amount of bone; design a three-dimensional image of the custom dental implant based on the shape of the natural extraction socket, the three-dimensional image of the custom dental implant having (i) an occlusal facing portion for receiving a restoration or forming an integral part of the restoration, (ii) a mid-portion featuring a contoured shape to mimic the natural profile of gingival emergence for optimal aesthetics, (iii) a bottom portion including one or more prongs and (iv) at least one energy storing device, the at least one energy storing device being provided along or integrated into the three-dimensional image of the custom dental implant, wherein a structure of the at least one energy storing device is based on information such as the tooth number or location of the tooth replacement, the contours and geometry of the alveolar bone, the amount of periodontal ligament fibers present, the initial stability required after implant placement, location of any neighboring nerves or other sensitive dental anatomy, and quality or quantity of bone required for the support of a dental implant device such that the at least one energy storing device deflects during insertion into the natural extraction socket expands to provide external pressure to stabilize the custom dental implant in the natural extraction socket during osseointegration.

Further features and advantages, as well as the structure and operation of various embodiments herein, are described in detail below with reference to the accompanying drawings.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Different ones of the Figures may have at least some reference numerals that may be the same in order to identify the same components, although a detailed description of each such component may not be provided below with respect to each Figure.

DETAILED DESCRIPTION OF THE INVENTION

Custom Dental Implant.

In accordance with example aspects described herein, a custom dental implant may be realized.

A natural tooth may be embedded in its natural socket. It may include pulp that may hold nerves and blood vessels and may be surrounded by dentine, which may be covered with enamel. Root portions of the tooth may have a thin layer of cement providing connection to ligaments, which anchor the tooth to jawbone. During implantation, an implant may be inserted into a hole in the jawbone.

According to an embodiment of present invention, a custom dental implant 1 may be individually shaped and integrated into the natural extraction socket of a patient. Preferably the custom dental implant 1 may be integrated into periodontal ligaments of the natural extraction socket or into the jaw bone. The shape of the portions of the implant 1 representing the root may be configured to copy or substantially copy the natural root of the tooth that was located in the natural extraction socket. Said shape, however, may be modified in order to provide pressed or barbed fit with the natural socket. Moreover the natural extraction socket may be surgically adapted before implantation. For example, damaged and infected soft tissue, tooth or bone substances may be removed in a reshaping step and a resulting shape of the extraction socket may be used in creating the custom dental implant 1. Preferably, said reshaping is minimal. The term "natural extraction socket" may hereinafter be used to refer to both a shaped and unshaped extraction sockets. Herein the custom dental implant 1 may remove the requirement of multiple drilling sequences and the implant may be placed at the same time as tooth extraction with minimal modification to the socket therefore simplifying the overall implant procedure from both a patient and clinician perspective.

Figure 1A:
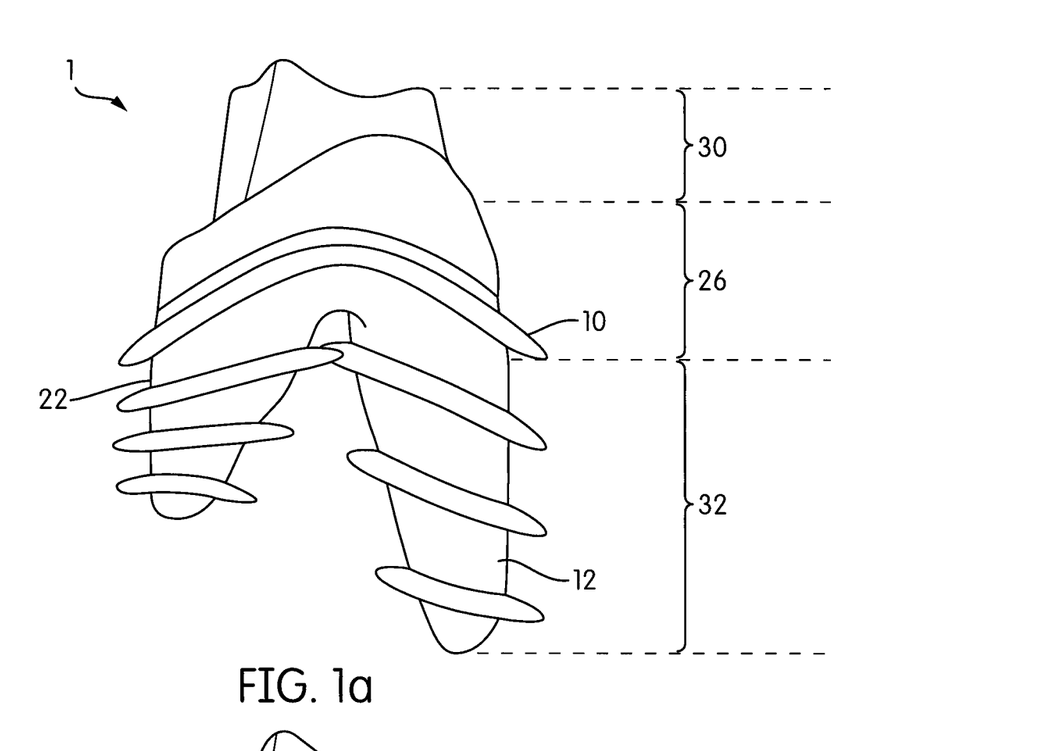
FIG. 1a is a perspective view illustrating an exemplary embodiment of the present invention.

The custom dental implant 1 may include a spring-like energy storing device/mechanism 10 to assist in implant installation while also providing initial stability (e.g. rotational and/or lateral stability) until osseointegration is completed. Herein, the custom dental implant 1 may include one or more energy storing devices 10 disposed around an exterior surface 22 of the implant 1 as shown in FIG. 1a. The custom dental implant 1 may comprise a single material such as ceramic but may also be either a one or multiple piece system to facilitate manufacturability and ease of use. In an embodiment herein, the one or more energy storing devices 10 may rely on the principle of elastic potential energy. An object, item, or feature may deform in an elastic manner and the result of the deformation may be the conversion of this movement into potential energy. This may be simulated or explained by the movement of a simple linear spring. The elastic potential energy stored in a spring can be modeled after Hooke's law, where the restoring force exerted by a spring is proportional to the length of its deflection. This is modeled in the equation $F=-k*x$. Additionally, the energy stored in more complex geometries, like beams or cantilever arms or varying thickness and width, may be modeled using equations that include various material properties like the Modulus of Elasticity along with the moment or inertia of the shape.

Figure 2:
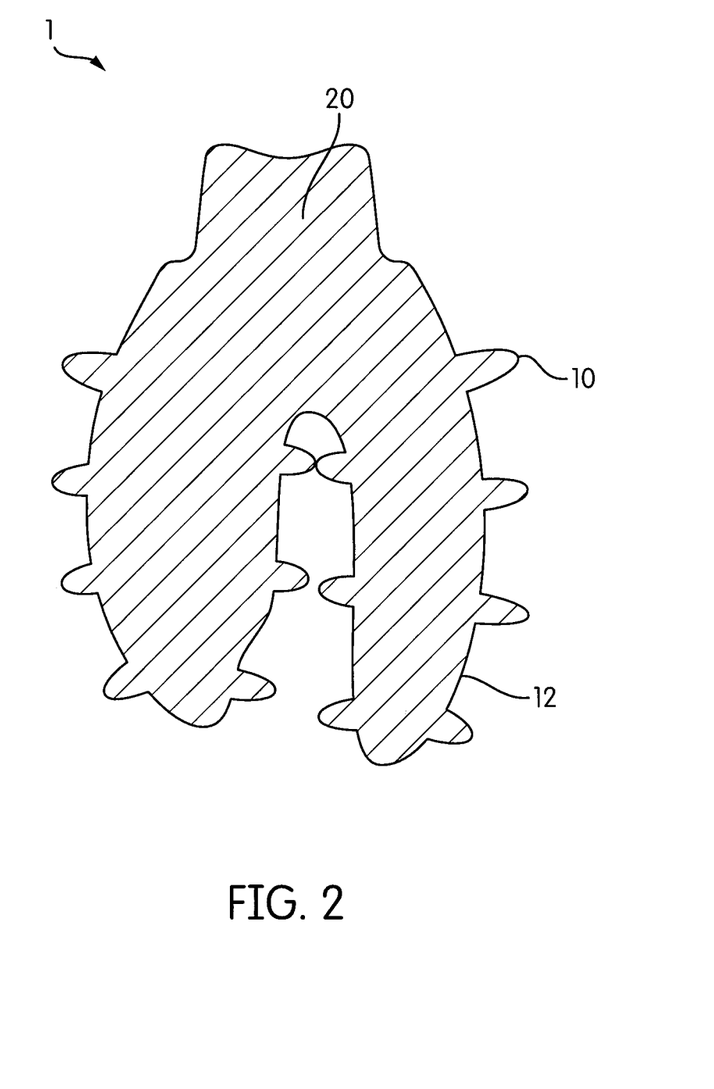
FIG. 2 is a cross sectional view illustrating a cross section of an exemplary embodiment of the present invention.
Figure 5:
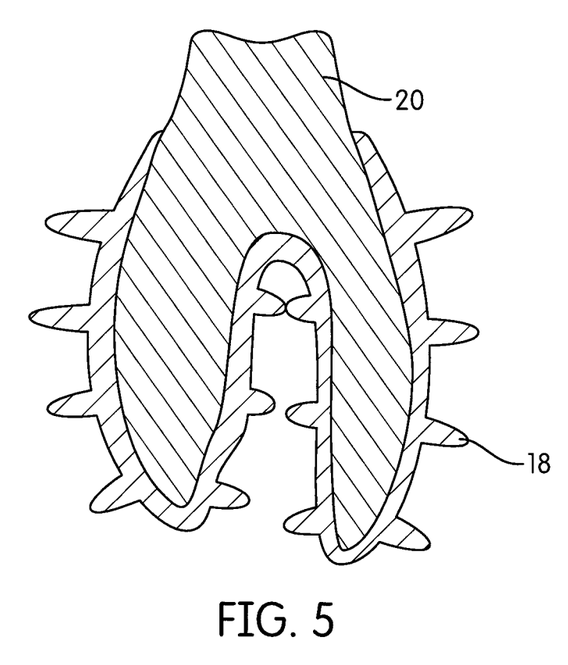
FIG. 5 is a cross sectional view illustrating a cross section of another exemplary embodiment of the present invention.
Figure 6:
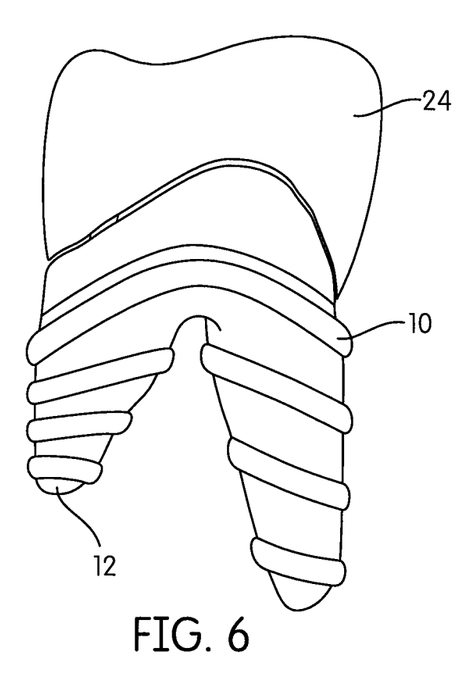
FIG. 6 is a perspective view showing an embodiment of the present invention having a crown.
Figure 9A:
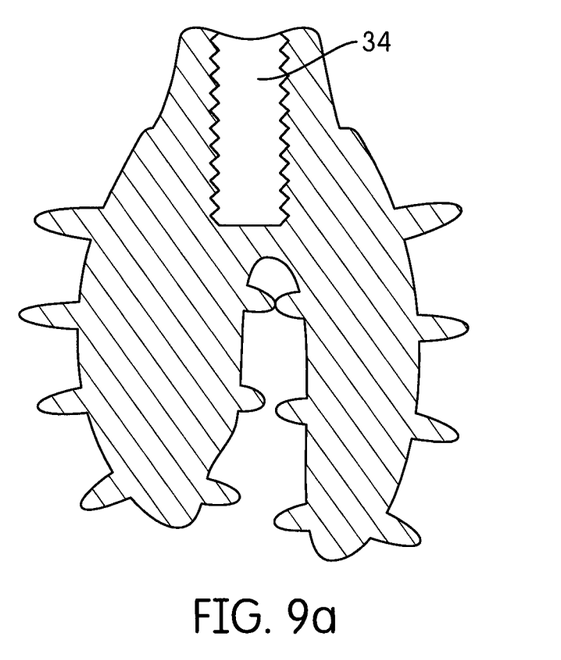
FIG. 9a is a cross sectional view illustrating a cross section of an exemplary embodiment of the present invention having a first configuration of the internal portion.
Figure 9B:
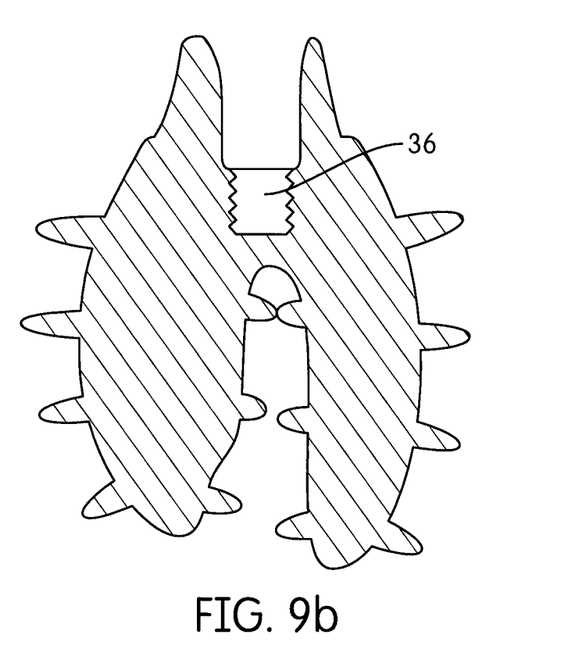
FIG. 9b is a cross sectional view illustrating a cross section of an exemplary embodiment of the present invention having a second configuration of the internal portion.
Figure 9C:
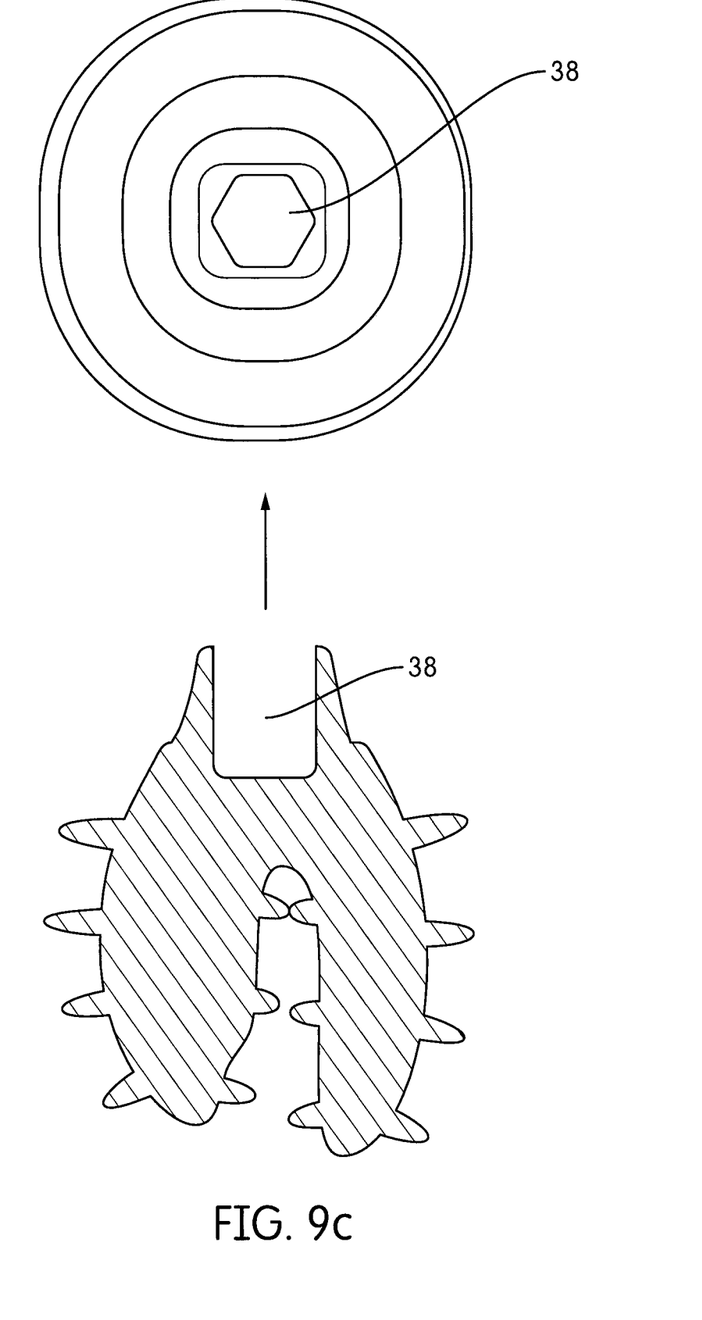
FIG. 9c is a cross sectional view illustrating a cross section of an exemplary embodiment of the present invention having a third configuration of the internal portion and illustrating a top view of said third configuration.

In an embodiment herein, the energy storing device 10 may be an extension of the exterior surface 22 of the custom dental implant 1 and thus may be made of the same material (e.g. ceramic) as the internal portion 20 of the custom dental implant 1 (FIG. 2). Moreover, the overall shape of the implant 1 may be larger than the natural extraction socket. This is due to the need for the energy storing features to deform in order to achieve the initial stability required. The shape of a bottom/apical portion 32 of the implant 1 may follow the contours of the extraction socket but may exceed the volume of the socket due to the design and inclusion of the energy storing features (i.e. exterior surface 22 may follow the contour of the socket and energy storing device 10 may extend beyond this said contour.) In another embodiment according to the present invention, the energy storing device 10 may be a part of or may be the outer shell 18 of the custom dental implant 1 wherein an internal component 20 of the custom dental implant may fit or may be fused with the outer sleeve 18 (FIG. 5). In an embodiment herein, the internal component 20 may have a straight wall or reverse tapered fit and may include no undercuts so the internal component may fit in/be inserted easily into the outer sleeve 18. In a further exemplary embodiment, titanium and ceramic materials of the implant 1 may be fused together. Titanium may be used because of its favorable biocompatibility and mechanical properties. This includes the strength of the material, osseointegration performance, and elasticity. Ceramic may be used because of its aesthetic appearance, biocompability, and favorable soft tissue attachment. The ceramic and titanium may be fused together using various high temperature bonding techniques or even through the use of cement or mechanical locking features like grooves, slots, or notches. In another embodiment herein the internal portion 20 may extend into an occlusal facing portion 30 said internal portion 10 being configured to provide support for a restoration 24 or be an integral part of said restoration 24 (FIGS. 1a and 6). FIGS. 9a-9c show further configurations 34, 36 and 38 of the internal portion 20. The internal portion may not necessarily align in any specific orientation or axis relative to the implant. For example, the orientation of the internal portion 20 may be along a vertical implant axis, however the internal portion 20 may also be oriented at other locations of the implant 1 where the material wall thickness is sufficient enough to provide support. Moreover, this internal portion 20 may also be oriented such that it may mate with a dental restoration in a way to an angulated screw channel concept, where the screw access hole is hidden from the aesthetic point of view, i.e. lingual side. The energy storing device 10 may be, for example, a spring, coil, barb, and/or other means that may be configured to (i) provide or substantially provide the flexibility needed to install the implant, and/or (ii) store enough energy to provide initial stability after installation. Herein, for example a spring stiffness rate may be between 2-50 lbs/in. By assessing the implant site and determining for example, an initial stability required, an amount of flexibility of the energy storing means may be obtained. The initial stability may be determined based on the quality and quantity of bone and whether or not the preparation site is a candidate for immediate loading as determined by for example, the clinician. In an embodiment herein, using the Osstell ISQ scale for measurement, this can vary between 60 to greater than 70. The amount of flexibility required in the energy storing system for the implant system can be calculated using computer modeling such as with Finite Element Analysis or other simulation programs. The energy storing device 10 may deflect during installation of the implant 1 allowing for less overall force required to install the implant than the force used to install conventional implants. After insertion, the energy storing device 10 may then expand and provide external pressure towards the walls of the dental root form to achieve stability.

Figure 3:
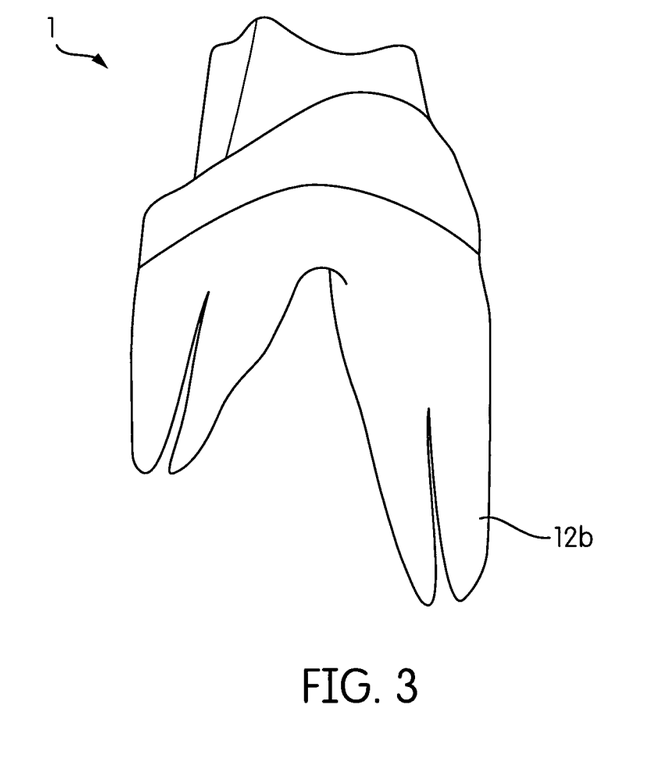
FIG. 3 is a perspective view illustrating another embodiment of the present invention.
Figure 4:
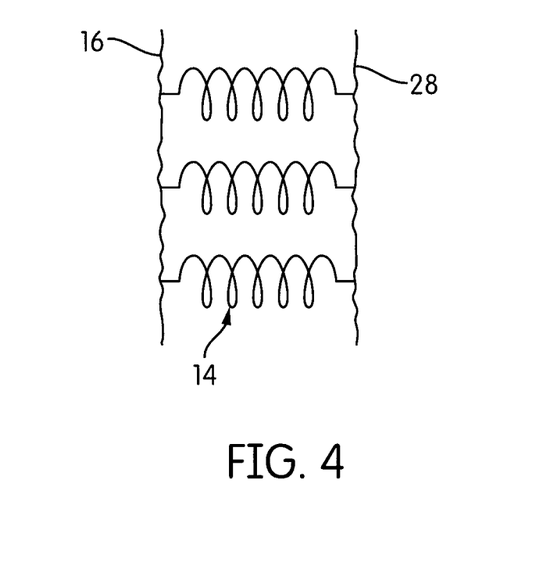
FIG. 4 is a side view illustrating yet another embodiment of the present invention.

In an embodiment of the present invention, the energy storing device 10 may be integrated into the design of the bottom/apical portion 32 of the implant 1 wherein, where each prong 12 (portions of the custom dental implant representing the root) of the implant 1 may be constructed to be flexible in order to bend during installation as shown in FIG. 3. The bending of the energy storing device 10 may be confined in the elastic portion of the material to ensure that the implant 1 is able to store the potential energy. If the energy storing device 10 is not able to withstand the deflection without plastic failure, the implant may not be able to function properly. In yet another embodiment, as shown in FIG. 4, a harness comprising a tessellated interface 14 may be configured to join the socket walls 16 and the walls of a standard ceramic dental implant 28. The harness may be part of the customized dental implant 1 and may interface with the socket walls 16.

In an alternate embodiment, the implant 1 may include similar "energy storing" properties but the implant 1 and/or the energy storing device 10 may be manufactured from a resorbable structural material such as hydroxyapatite, tricalcium phosphate, magnesium etc. These embodiments may be made of a ceramic or metallic material and additional features such as a porous or micro structured surface may be included to enhance osseointegration and promote bone regeneration functions, replacing the need for secondary graft materials to be used during surgery/installation.

Method for Making a Custom Dental Implant

Figure 7:
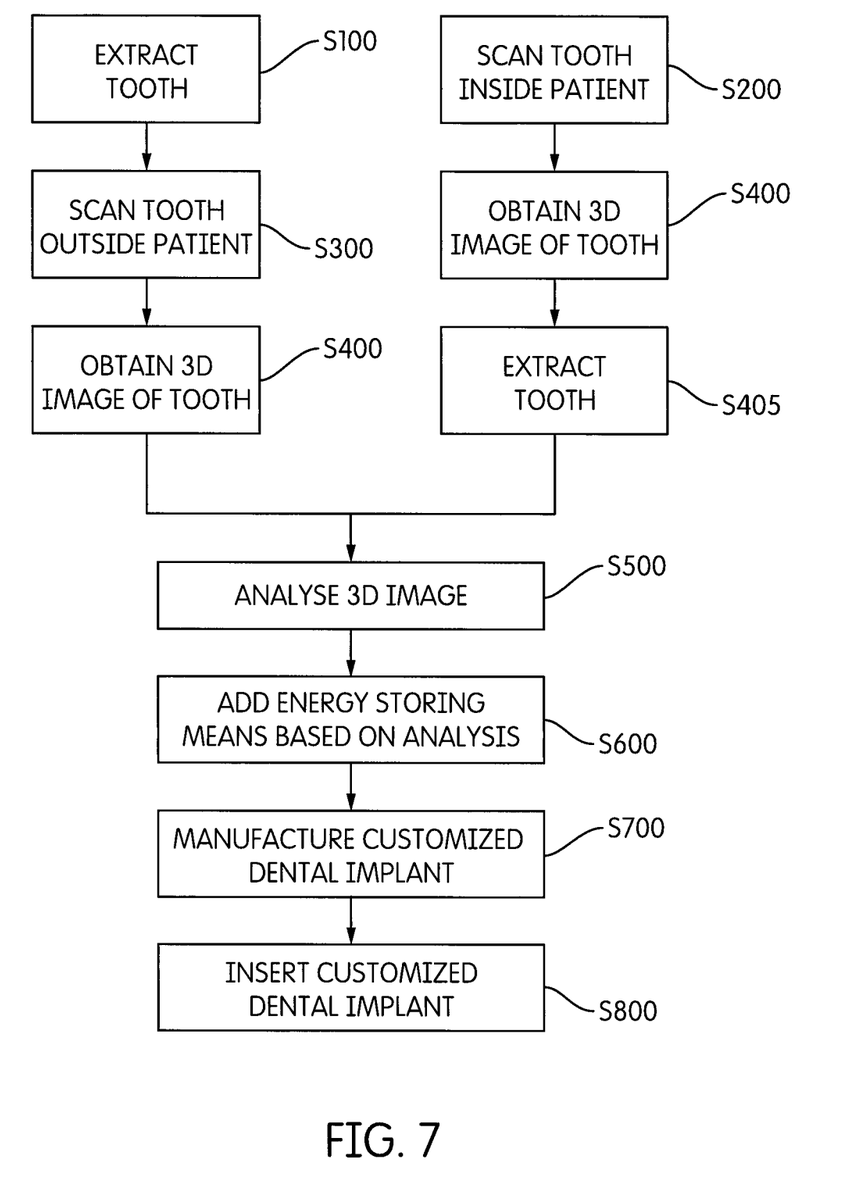
FIG. 7 is a flow chart showing an exemplary method of the present invention.

Having described the custom dental implant of FIG. 1, a method of making the custom dental implant will now be further described in conjunction with FIG. 7.

Turning now to FIG. 7, a custom dental implant 1 may be shaped and integrated into a natural extraction socket of a patient. The shape of prongs 12 may match or substantially match the natural root of the tooth that was located in the socket. In an embodiment of the present invention, the method of creating the custom dental implant 1 may include the steps of (i) scanning the anatomical shape of the patient's tooth or dentition; (ii) obtaining a three-dimensional (3D) representation of the tooth as data record; and (iii) manufacturing of the custom dental implant 1 based on the three-dimensional data obtained. In an embodiment herein, the scanning may be performed before extraction of the tooth. In another embodiment herein, the scanning step may be performed after extraction of the tooth as discussed hereinafter.

In Step S100, the tooth to be replaced may be extracted and cleaned. The extracted tooth may then be scanned in Step S300 to obtain a 3D image of the extracted tooth Step S400. Alternatively the tooth may be scanned prior to extraction using Computer Tomography (CT), Cone Beam Computed Tomography (CBCT) or Magnetic Resonance Imaging (MRI), intraoral scanning or the like wherein surface descriptions, such as in STL-format, or volumetric data, such as in "voxel"-format may be transformed into a 3D representation of the tooth.

After obtaining the 3D Image of the tooth in Step S400, the tooth may be extracted in Step S405 if not already extracted. An image of the socket may also be obtained directly. The 3D Image may then be analyzed in step S500 to obtain information about the tooth and/or the natural extraction socket for use in designing the energy storing device 10. The information may include (i) size/shape of the natural extraction socket, location of neighboring dental anatomy, amount of remaining periodontal ligament, location of nerves, density of surrounding bone, soft tissue geometry and profile, and depth or amount of bone (ii) energy needed to provide a stable implant. (iii) anatomy of implant required (iv) optimal geometry of implant and energy storing features.

Figure 1B:
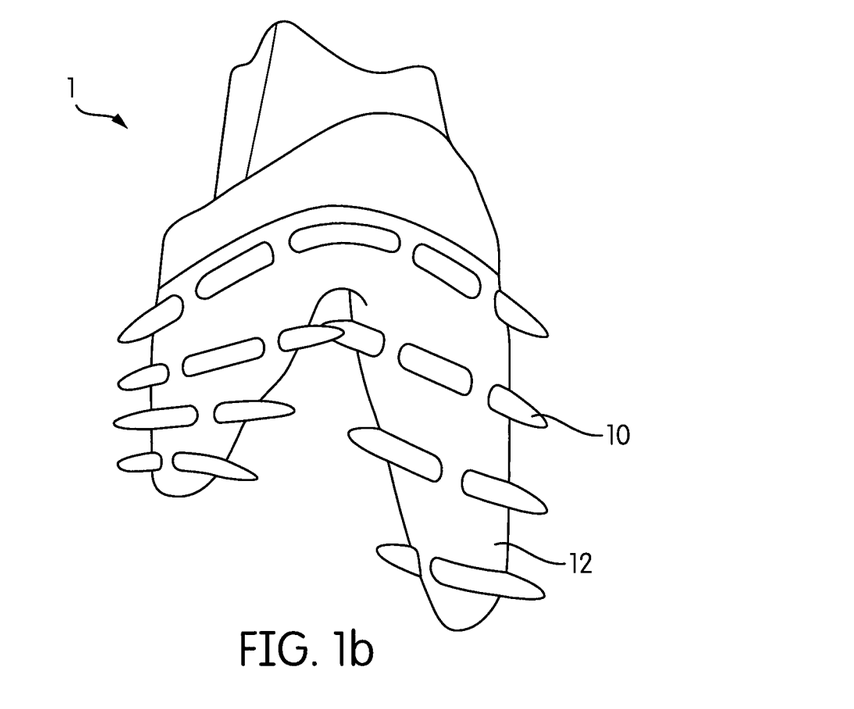
FIG. 1b is a perspective view illustrating another exemplary embodiment of the present invention.

After said analysis, the one or more energy storing devices 10 may be designed based on the obtained information, Step S600. The design may be such that each energy storing device 10 may fully or partially surround a mid-section 26 and/or prongs 12 at a bottom section 32 of the custom dental implant 1 to provide deflection and stability as shown in FIGS. 1a and 1b. The mid-section 26 may be configured to have a predetermined emergence profile that may correspond to an emergence profile of the patient being treated. In another exemplary embodiment of the present invention, the design may be such that the prongs 12 of the implant may be divided into various beam-like geometries (microprongs) 12b (FIG. 3) to allow for deflection during installation. In an exemplary embodiment herein, the prongs 12 may be beams oriented vertically along the implant installation access and the micro-prongs 12b may be optimized to achieve the ideal implant stability and stiffness required as described by protocols such as the ISQ and/or other stability measurements.

The internal portion of the implant 20 may be designed to mimic existing screw form dental implant designs, including such features as an anti-rotation feature, female threads, and a connection for additional prosthetic options as shown in FIGS. 9a-9c. Said features may be on a different axis or the same axis as a center axis of the implant 1. Moreover, due to the custom, patient specific nature of the implant 1, some of these restorative components may be integrated into the design of the custom dental implant 1 by designing an upper portion of the implant to fit an ideal crown as determined by the cosmetic need and the neighboring dental anatomy.

In yet another exemplary embodiment of the present invention, the design may include a "harness" such as a tessellated spring structure/interface 14 between walls of the natural extraction socket 16 and walls of a standard dental implant 28. The tessellated spring structure may be configured to provide spring loading for installation and stability, but may also feature materials (such as calcium phosphate, hydroxyapatite, magnesium, and other bioresorbable materials) and geometry to serve as a graft to promote bone growth. Moreover each prong 12 of the implant 1 may have a built in spring or beam like features to act as a cantilever, allowing for movement along a predetermined axis. This may function by adding compliance in the undercut features to allow flexibility during insertion.

After the design, the custom dental implant 1 may be manufactured as shown in Step S700. It may be manufactured using additive manufacturing methods alone, or a combination of additive, subtractive methods and/or molding methods. It may be manufactured produced by milling, grinding or rapid prototyping, for example, at a dentist's office or in a laboratory or at a centralized manufacturing location. It may also be produced using conventional laboratory procedures such as, for example, casting. In an embodiment herein, the restoration 24 may be manufactured using standard procedures in the art.

In addition, the custom dental implant may be coated with a thin layer of biocompatible material that is suitable to be integrated into and adopted by the existing periodontal ligament cell structure of an individual patient.

It should be noted that the methods described herein may be fully and/or partially automated. After manufacturing the custom dental implant 1, it may be inserted/implanted into the extraction socket as shown in Step S800.

Computer System for Making a Custom Dental Implant

Figure 8:
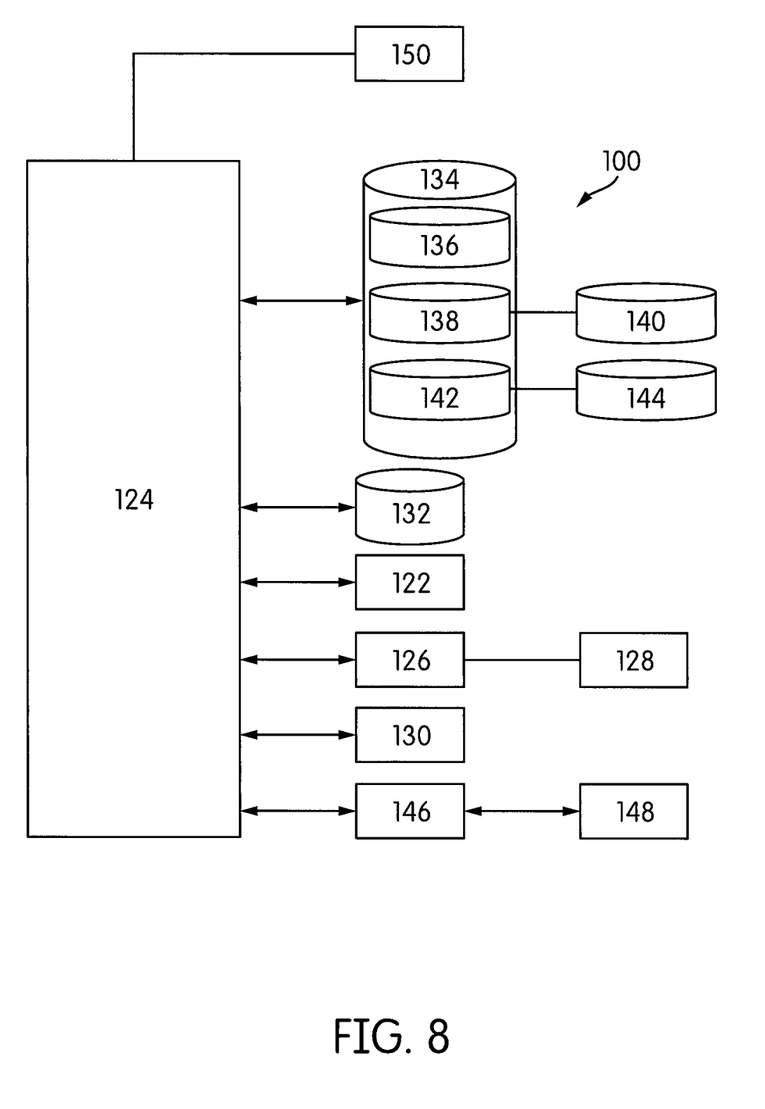
FIG. 8 is a block diagram showing a computer system according to exemplary embodiment of the present invention

Having described a custom dental implant 1, reference will now be made to FIG. 8, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

The computer system 100 may include a scanner such as CBCT, MRI and/or intra-oral scanner for obtaining 3D images of the tooth to be replaced. The computer system may also include at least one computer processor 122. The computer system may be configured to receive the 3D images and the processor 122 may be configured to analyze said 3D images in order to create the custom dental implant and corresponding one or more energy storing devices 10 which may be rendered on a display 128 of the computer system 100. In an embodiment herein the computer system 100 may take input from a clinician through an input unit such 130 such as a keyboard, mouse, touchscreen monitor or the like in order to create a finished custom dental implant 1. The processor 122 may be connected to a communication infrastructure 124 (e.g., a communications bus, a cross-over bar device, or a network).

A display interface (or other output interface) 126 may forward video graphics, text, and other data from the communication infrastructure 124 (or from a frame buffer (not shown)) for display on the display unit 128.

One or more steps of creating the custom dental implant 1 may be stored on a non-transitory storage device in the form of computer-readable program instructions. To execute a procedure, the processor 122 loads the appropriate instructions, as stored on storage device, into memory and then executes the loaded instructions.

The computer system 100 may also comprise a main memory 132, which may be a random access memory ("RAM"), and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods described. Accordingly, the computer programs may control the computer system 100.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, may cause the computer system 100, to perform all or some of the methods described herein.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

What is claimed is:

1. A method of comprising the steps of;
   assessing an implant site of a patient to determine an initial stability required, for a custom spring-loaded dental implant, based on at least a quality and quantity of alveolar bone of the patient;
   computing, responsive to said assessing, an amount of flexibility required for at least one flexible energy storing device of the custom spring-loaded dental implant;
   receiving three-dimensional data representing a shape of a natural extraction socket of a tooth of the patient;
   analyzing the three-dimensional data to obtain information about characteristics of the natural extraction socket;
   designing a three-dimensional image of the custom spring-loaded dental implant based on the characteristics of the natural extraction socket, the designing step including designing the three-dimensional image of the custom spring-loaded dental implant to have (i) an occlusal facing portion for receiving a restoration or forming an integral part of the restoration, (ii) a mid-portion configured to have a desired emergence profile, (iii) an apical portion including one or more prongs and (iv) the at least one flexible energy storing device,
   designing the at least one flexible energy storing device to be along or integrated into the custom spring-loaded dental implant and having the computed flexibility,
   wherein said designing step of the at least one flexible energy storing device is based on information selected from the group consisting of (i) location of the tooth replacement, (ii) geometry of the alveolar bone, (iii) amount of periodontal ligament fibers present, (iv) initial stability required after implant placement, (v) location of neighboring nerves and (vi) quality or quantity of bone required for support of the custom spring-loaded dental implant
   wherein the method further comprises:
   fabricating the custom spring-loaded dental implant based on said designing step: and
   inserting, responsive to the fabricating, the fabricated custom spring-loaded dental implant into said natural extraction socket, without said inserting altering the shape of the natural extraction socket, by the at least one flexible energy storing device substantially deflecting in a spring-like manner during insertion and therefore allowing for less overall force to install the custom spring-loaded dental implant than the force used to install conventional implants, and subsequently expanding to provide external pressure to stabilize the custom dental implant in the natural extraction socket during osseointegration.

2. The method according to claim 1, further comprising scanning the tooth to obtain said shape of the natural extraction socket prior to receiving the three-dimensional data.

3. The method according to claim 2, further comprising scanning the tooth before extracting said tooth.

4. The method according to claim 2, further comprising scanning the too after extracting said tooth.

5. The method according to claim 2, further comprising performing the scanning step with a Computer Tomography (CT) machine, Cone Beam Computed Tomography (CBCT) machine, intraoral digital scanner and/or Magnetic Resonance Imaging (MRI) machine.

6. The method according to claim 1, further comprising designing the at least one flexible energy storing device to fully or partially surround the mid-section and or prongs of the custom dental implant.

7. The method according to claim 1, further comprising designing an internal portion of the custom dental implant to mimic anti-rotation features, threads and/or connection geometries of screw form dental implants to support a restoration.

8. The method of claim 1, wherein the computing is carried out using a finite element analysis.

9. The method of claim 1, further comprising fabricating the at least one flexible energy storing device with a material that withstands plastic failure.

\* \* \* \* \*